United States Patent [19]

Chevallet

[11] Patent Number: 4,889,635

[45] Date of Patent: Dec. 26, 1989

[54] METHOD AND APPARATUS FOR CONTROLLING THE QUANTITIES OF LIQUID CIRCULATING IN THE DIALYSIS LIQUID CIRCUIT OF AN ARTIFICIAL KIDNEY

[75] Inventor: Jacques Chevallet, Serezin du Rhone, France

[73] Assignee: Hospal Industrie, Cedex, France

[21] Appl. No.: 42,878

[22] Filed: Apr. 24, 1987

[30] Foreign Application Priority Data

Apr. 25, 1986 [FR] France .............................. 86 06225

[51] Int. Cl.⁴ .............................................. B01D 13/00
[52] U.S. Cl. ...................................... 210/646; 210/87; 210/321.71
[58] Field of Search .................... 210/321.71, 646, 87; 73/3

[56] References Cited

U.S. PATENT DOCUMENTS

| | | | |
|---|---|---|---|
| 3,598,727 | 8/1971 | Willock | 210/321.71 |
| 3,946,731 | 3/1976 | Lichtenstein | 128/214 R |
| 4,606,826 | 8/1986 | Sano et al. | 210/646 |
| 4,747,950 | 5/1988 | Guinn | 210/646 |
| 4,769,134 | 9/1988 | Allan et al. | 210/87 |

FOREIGN PATENT DOCUMENTS 209118 10/1985 Japan ........................................ 73/3

Primary Examiner—Bernard Nozick
Attorney, Agent, or Firm—Finnegan, Henderson, Farabow, Garrett & Dunner

[57] ABSTRACT

The invention relates to an artificial kidney for controlling and maintaining parity of the entering and emerging quantities in the dialysis liquid circuit. The artificial kidney comprises a dialysis liquid circuit having on either side of the haemodialyser a sensor capable of measuring the quantity of the circulating liquid and a pump for displacing the said dialysis liquid. A microprocessor controller for comparing the quantities of liquid circulating in the upline sensor with the quantities of liquid circulating in the downline sensor, the controller is used for maintaining the quantities of liquid circulating in the upline sensor equal to the quantities of liquid circulating in the downline sensor, during the same period, by subjecting the operation of the pump for displacing the dialysis liquid to the result of the comparison determined by the controller.

18 Claims, 4 Drawing Sheets

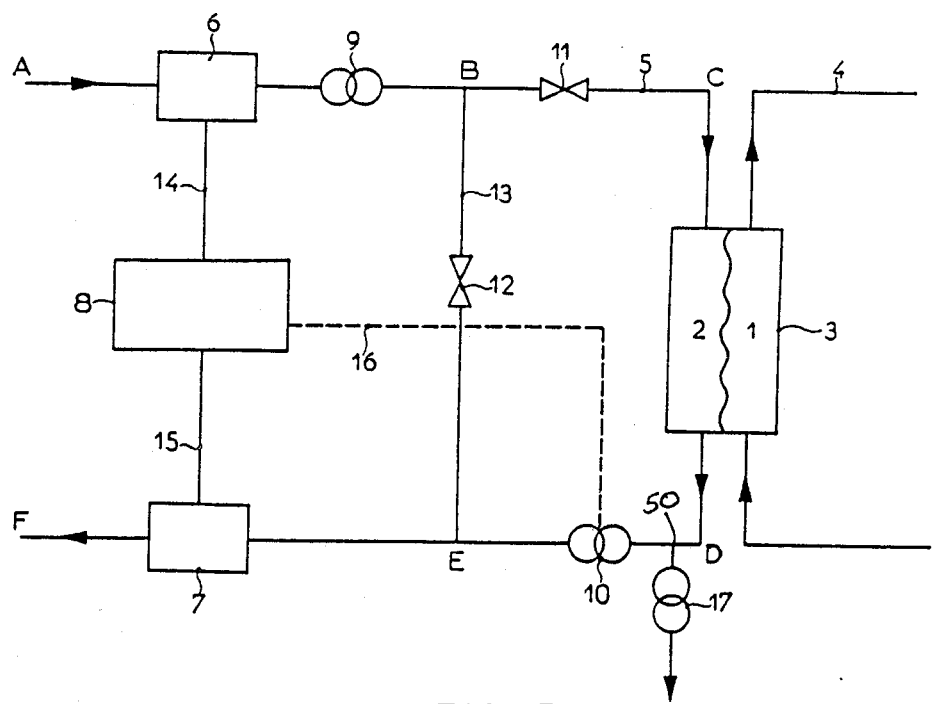
FIG. I
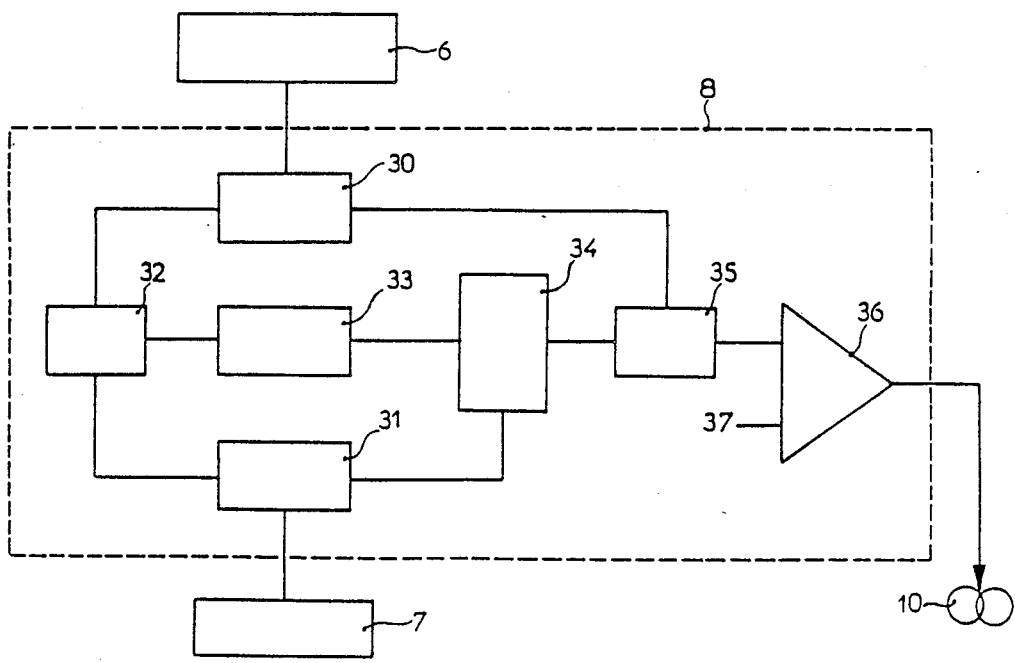
FIG. II

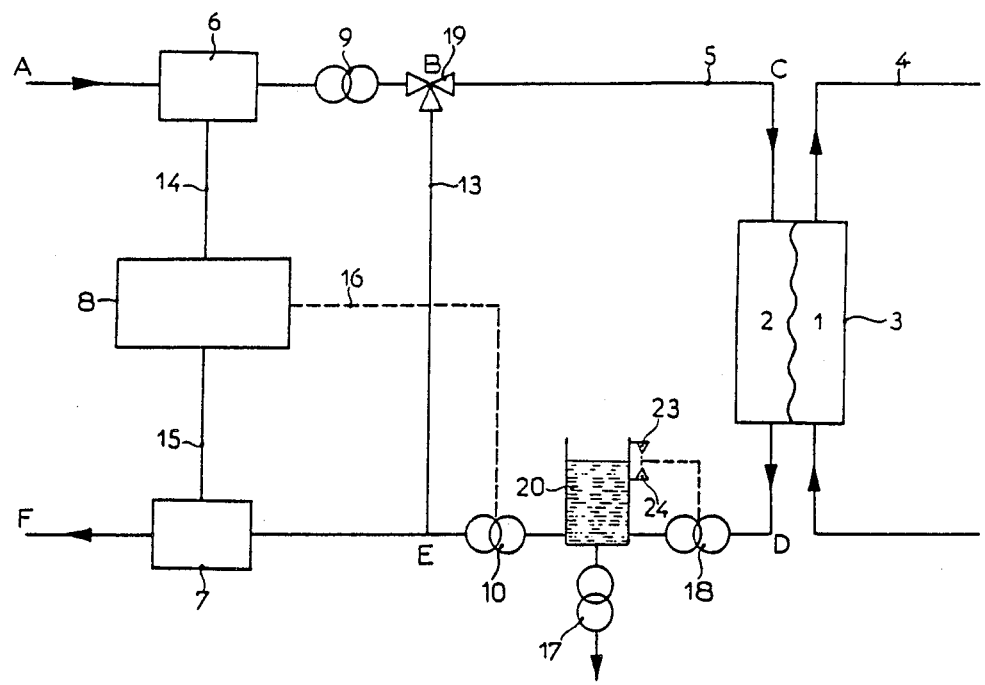
FIG. III
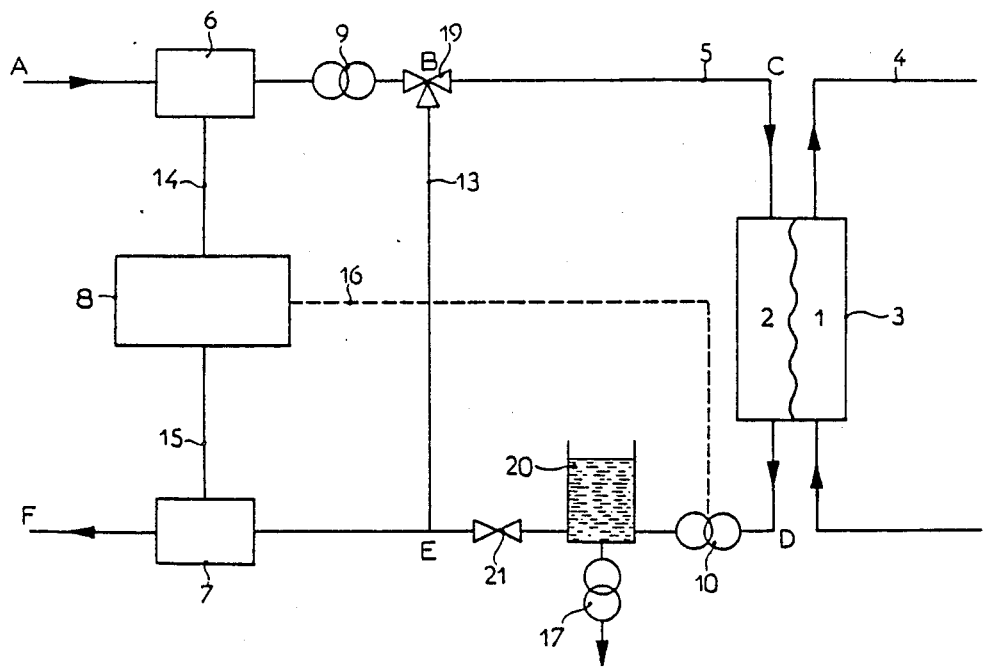
FIG. IV

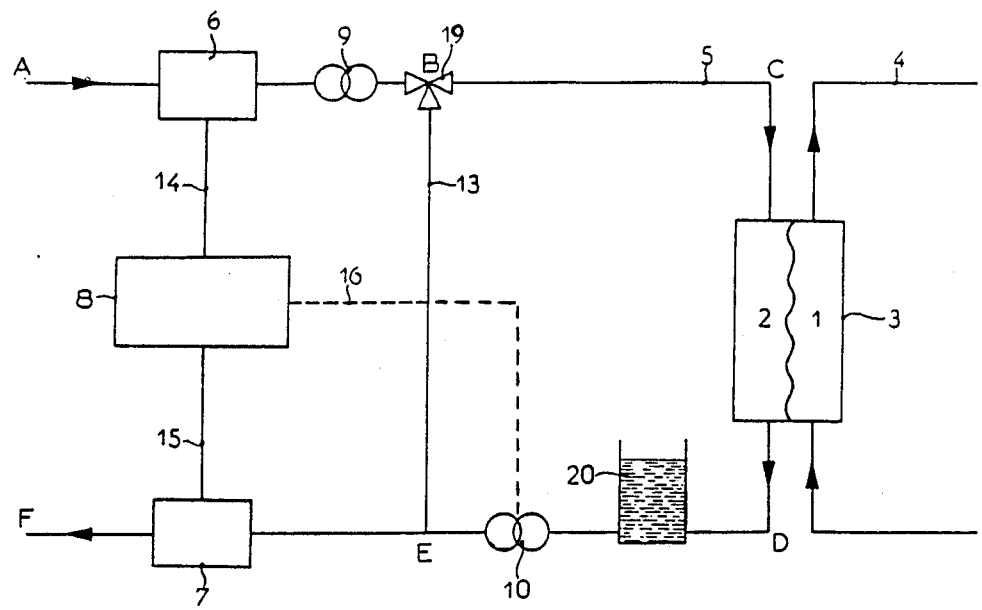
FIG. V
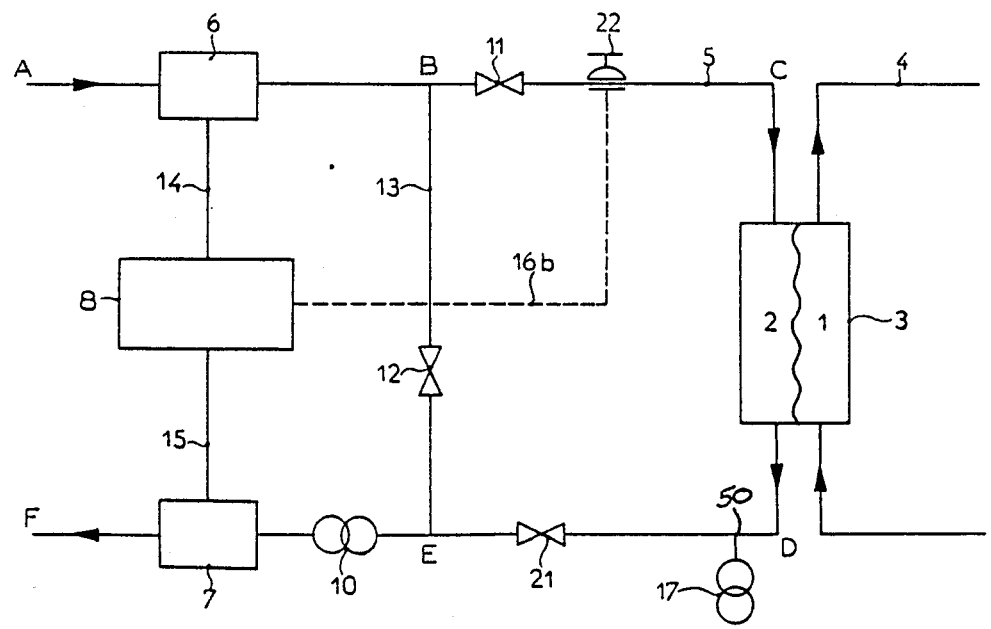
FIG. VI

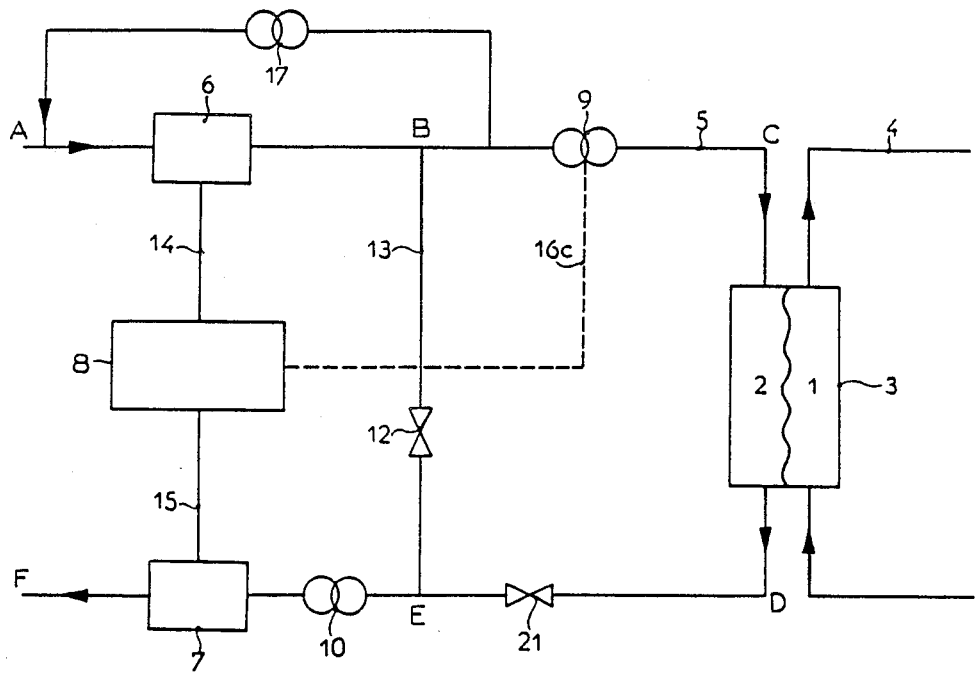
FIG. VII

METHOD AND APPARATUS FOR CONTROLLING THE QUANTITIES OF LIQUID CIRCULATING IN THE DIALYSIS LIQUID CIRCUIT OF AN ARTIFICIAL KIDNEY

BACKGROUND OF THE INVENTION

1. Field of the Invention

The present invention concerns an artificial kidney used in the extracorporeal treatment of blood, and in particular, in the treatment of blood by dialysis and by ultrafiltration. The present invention concerns more particularly an artificial kidney allowing the ultrafiltration of the blood to be controlled with great accuracy during a haemodialysis session.

The present invention also concerns a method for controlling and maintaining parity in the quantities of the dialysis liquid entering into and emerging from a dialysis liquid circuit of an artificial kidney.

2. Description of the Related Art

Artificial kidneys capable of controlling ultrafiltration of blood are known in the prior art. The article "Volumetrical Microcomputer Based Ultrafiltration Monitor For Hemodialysis" by J. M. P. Wokke, *The International Journal of Artificial Organs*, vol. 8 No. 1, 1985, describes an artificial kidney with a dialysis liquid circuit which comprises two flowmeters, one upline, the other downline from the haemodialyser. As a result of the pressure gradient obtained on either side of the semi-permeable membrane of the dialyser, a fraction of the liquid present in the blood passes by ultrafiltration through the membrane. The amount of flow of the dialysis liquid measured downline from the haemodialyser then exceeds the amount of flow measured upline from the haemodialyser. The difference in the measurement of the dialysis liquid flow downline and that of the dialysis liquid flow upline is considered to correspond to the ultrafiltration flow. In such a system, the errors inherent in the flowmeters are partly corrected by a calibration obtained by by-passing the haemodialyser and by letting the same flow of dialysis liquid circulate in the two flowmeters. When the apparatus is operating normally, that is to say, when ultrafiltration occurs, the amount of flow measured downline from the haemodialyser is no longer only the dialysis liquid flow but is the sum total of the dialysis liquid flow and the flow of the ultrafiltrate. The measurement of the downline flow then lacks accuracy because the correction effected by calibration is only valid for a specific value of flow equal to that during calibration. Further compounding errors resulting from the absence of calibration during ultrafiltration, are errors inherent in controlling the amount of blood passed through the dialyser during ultrafiltration.

U.S. Pat. No. 3,946,731 to Lichtenstein, discloses an artificial kidney comprising in series over the dialysis liquid circuit a reservoir for the dialysis liquid, an upline pump, an upline flowmeter, a haemodialyser, a downline flowmeter, and a downline pump. A device for collecting the ultrafiltrate is placed in parallel between the flowmeter and the downline pump and this device is intended to receive the excess of the dialysis liquid corresponding to the ultrafiltrate coming from the blood. In such an apparatus, the downline and upline pumps are operated synchronously in such a way that they deliver the same quantities of dialysis liquid at the inlet and outlet of the dialysis liquid circuit, save for the accuracy of the pumps. The apparatus and method disclosed in Lichenstein for controlling the ultrafiltration has inherent inaccuracies in flow monitoring because errors in the measurement of the ultrafiltration result from the inaccuracies of each of the upline and downline flowmeters as well as measurement errors in the parity of the quantity of dialysis liquid delivered by the pumps disposed upline and downline from the haemodialyser. Current market demands for haemodialysors require that the device be able to measure the quantities of the dialysis liquid at the input and output of the dialysis liquid circuit in the range of plus or minus 30 ml/hour. The ultrafiltration measurement apparatus and method taught by Lichenstein does not afford such accuracy over the control of the ultrafiltration.

It is therefore an object of the present invention to provide an artificial kidney which does not have the drawbacks of the prior art and is capable of controlling the ultrafiltration of blood during a haemodialysis session in a very accurate manner, or at least within plus or minus 30 ml/hr.

Another object of the present invention is to provide an artificial kidney comprising a portion of a dialysis liquid circuit wherein, whether there is or is not ultrafiltration of the dialysis liquid, the quantity of the entering dialysis liquid is kept equal to the quantity of the emerging liquid with very great accuracy.

It is a further object of the present invention to provide an artificial kidney and method of operating the same capable of compensating for the inherent errors in the sensors used for measuring the quantities of the circulating dialysis liquid.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

SUMMARY OF THE INVENTION

To achieve the foregoing objects, and in accordance with the purposes of the invention as embodied and broadly described herein, an artificial kidney is provided comprising a haemodialyser containing at least a first and a second compartment separated by a semi-permeable membrane for permitting dialysis and ultrafiltration of the blood, the first compartment being connected to a patient by an extracorporeal blood circuit, and the second compartment being connected to a dialysis liquid circuit. The artificial kidney further includes means for displacing the dialysis liquid through the circuit, and an upline and downline sensing means, positioned on opposite sides of the second compartment in the liquid circuit, for measuring the quantity of dialysis liquid flowing upline and downline of the haemodialyser and generating signals in accordance with the measured flows. The artificial kidney further includes means for comparing the signals representative of flow in the upline sensing means and the flow in the downline sensing means during the same measurement period, and generating a signal in accordance with the comparison of the measured flows, and means for controlling the operation of the pump means to respond to the signal representative of the comparison of the quantities of dialysis liquid measured with the upline sensing means and the downline sensing means.

There is further provided a method for controlling and maintaining the parity of dialysis liquid quantities at the inlet and outlet of a dialysis liquid circuit connected to a haemodialyser, the dialysis liquid circuit having sensing means, positioned upline and downline of the haemodialyser, for measuring the quantity of the circulating dialysis liquid, and means for displacing the dialysis liquid, the method comprising the steps of measuring, with the upline sensing means, the quantity of dialysis liquid flowing in the liquid circuit; measuring, with the downline sensing means concurrently with measuring the flow in the upline sensing means, the quantity of dialysis liquid flowing in the liquid circuit; generating signals in accordance with the measured flows in the upline and downline sensing means; comparing the signals representative of the flow through the upline sensing means and the flow through the downline sensing means and generating a signal in accordance with the comparison of the measured quantities of dialysis liquid flowing; and controlling the operation of the pump means for displacing the dialysis liquid in response to the signal representative of the comparison of the quantities of dialysis liquid flowing through the upline sensing means and the downline sensing means.

It is further preferable that the artificial kidney in accordance with the present invention includes means for drawing off a portion of the dialysis liquid passing through the haemodialyser at an extraction connection positioned between the upline and downline sensing means.

In the case where the extraction means comprises a pump, for example, the combined action of this pump and means for displacing the dialysis liquid creates a lower pressure in the portion of the downline sensor circuit passing through the haemodialyser. This low pressure causes, if the circuit is non-deformable, the passing of a fraction of the liquid present in the blood through the semi-permeable membrane of the haemodialyser until the equilibrium between the pressures of the blood and of the dialysis liquid is re-established. The ultrafiltrate quantity thus obtained is then equal to the quantity of the dialysis liquid extracted from the circuit.

It is still further preferable that the artificial kidney include means for calibrating the sensors. By way of example and not limitation, the calibration may be effected by by-passing the haemodialyser and the ultrafiltration circuit by means of a by-pass circuit.

To facilitate an understanding of the invention, the sensing means disposed upline from the haemodialyser will be designated as the upline sensor and the sensing means disposed downline from the haemodialyser as the downline sensor.

An artificial kidney has now been invented, and it is this which achieves the objects of the present invention, which makes it possible to ensure the measurement and control of the dialysis liquid quantities circulating upline and downline from the haemodialyser with very great accuracy.

BRIEF DESCRIPTION OF THE DRAWINGS

The accompanying drawings, which are incorporated in and constitute a part of the specification, illustrate a presently preferred embodiment of the invention and, together with the general description given above and the detailed description of the preferred embodiment given below, serve to explain the principles of the invention.

FIG. I is a schematic diagram of a first embodiment of the artificial kidney in accordance with the invention;

FIG. II is a block diagram of a control device according to a first embodiment of the invention;

FIG. III is a schematic diagram of a second embodiment of the artificial kidney according to the invention; and FIGS. IV to VII are schematic diagrams illustrating additional embodiments of the artificial kidney according to the invention.

DESCRIPTION OF THE PREFERRED EMBODIMENT

Reference will now be made in detail to the present preferred embodiment of the invention as illustrated in the accompanying drawings.

Referring to FIG. I, it will be seen that the artificial kidney in accordance with the present invention comprises a haemodialyser 3 having a first compartment 1 connected to a patient by an extracorporeal blood circuit 4, and a second compartment 2 connected to a dialysis liquid circuit 5 having inlet A connected to a dialysis liquid source (not shown) and outlet F connected to an evacuation or recycling means (not shown).

Dialysis liquid circuit 5 comprises, upline from the haemodialyser 3, a sensing means 6 for measuring the quantity of the circulating dialysis liquid. In the present preferred embodiment, sensing means 6 also includes means for generating a pulse, for example on the passing of a predetermined amount of dialysis liquid. One may, for instance, choose a sensor which generates a pulse for each 0.08 ml of the circulating dialysis liquid passing therethrough. As embodied herein, sensing means 6 comprises a volumetric vane flowmeter, however, any suitable flowmeter may be used. One example of a sensor well suited to the present invention is a volumetric vane flowmeter, model T.I.T. 115 provided by the JENCON'S Company.

A means for displacing the dialysis liquid is positioned in the liquid circuit downline from sensor 6. As embodied herein, the displacement means comprises a pump 9. Pump 9 is preferably an occluding pump, but may be any pump of a known type, for instance a peristaltic pump or a gear pump or yet again a piston and valve pump.

A valve 11, or any other obturating device of a known type, is disposed downline from the pump 9 and upline from the haemodialyser 3.

In the portion of the dialysis liquid circuit downline from the haemodialyser, the circuit includes a second means for displacing the dialysis liquid. As embodied herein, the second displacement means comprises a circulating pump 10 which may be the same type of pump as pump 9.

A means for measuring the dialysis liquid flow is positioned downline from pump 10 in the liquid circuit. The measuring means comprises a sensor 7 disposed downline from the pump 10. Sensor 7 measures the quantity of the dialysis liquid circulating in this downline portion of the circuit. Advantageously, this sensor 7 may be of the same type as the sensor 6.

Although this is not preferential for the implementation of the present invention, one of the pumps 9, 10 or even both of them may be placed in the external portion of the dialysis liquid circuit, that is to say, in the portion of the circuit 5 upline from the sensor 6 and downline from the sensor 7.

With continued reference to FIG. I, the liquid circuit includes a means for isolating and by-passing haemodialyser 3. As embodied herein, the isolation means includes a by-pass tubing 13 disposed between the upline and downline portions of the dialysis liquid circuit, and a valve 11. This by-pass tubing 13 connects point B, situated downline from pump 9 and upline from the value 11, to the point E situated downline from the pump 10 and upline from the sensor 7. Together with the closing of valve 11, this by-pass tubing 13 makes it possible, for instance during calibration, to prevent the dialysis liquid from circulating in the haemodialyser 3 and the ultrafiltration circuit. By-pass tubing 13 is provided with a stop valve 12 or any other obturating device of a known type, so that during ultrafiltration, the valve 12 may be closed to insure the dialysis liquid passes through compartment 2.

The signals or pulses, representative of flow in the upline and downline sensors 6 and 7, respectively, which are generated by the sensors, are transmitted to a control device 8, which is jointed by a connection 14 to the upline sensor 6 and by a connection 15 to the downline sensor 7, and to pump 10 via connection 16. The regulation of the pump 10 by the control device 8 is represented by connecting line 16 in dashed lines.

The functions performed by the control device 8 will be better understood with the help of FIG. II, which represents, in the form of a block diagram, an example of a preferred embodiment of control device 8. The control device 8 includes means for counting the pulses emitted by the sensors 6 and 7. As embodied herein, the counting means comprises counters 30 and 31. Sensors 6,7 emit pulses which are counted or deducted by counters 30,31. A corrector 34 corrects the count values by a correction coefficient determined at the time of calibration by a computer 32 and stored in a memory circuit 33. The means for determining the correction coefficient will be discussed later. Preferably, the correction is only effected for one of the count values, the other count value being directly transmitted to a comparator 35. Comparator 35 then compares the number of pulses on the basis of the corrected value, supplied by each one of the sensors 6,7 and forwards an error signal to a monitor 36. Monitor 36 compares the error signal received with chosen reference 37 and controls the operation of the pump 10 so as to maintain the error signal equal to reference 37 and hence, the quantity of the dialysis liquid circulating in the upline sensor 6 equal to the quantity of dialysis liquid circulating in the downline sensor 7 during the same period. Thus, the instant invention provides real time monitoring, control and calibration of the flow of dialysis liquid.

In the case where the comparison in comparator 35 of the number of pulses emitted by upline sensor 6 and the number of pulses emitted by downline sensor 7 during the same period is effected on the basis of the difference of the two counts, the reference 37 is 0 zero. In the case where the comparison is effected by means of a ratio of the two counts, the reference chosen for the error signal is then 1. Preferably, control device 8 is a microprocessor.

The artificial kidney according to the instant preferred embodiment of the invention further includes a means for drawing off a portion of the dialysis liquid from an extraction connection. As embodied herein, the extraction means comprises a pump 17, preferably an occluding pump or a gear pump, which allows predetermined dialysis liquid quantities, measured by volume and/or flow, to be drawn off at the extraction connection 50. Extraction connection 50 of the dialysis liquid may be effected at any point of the circuit 5 between the upline and downline sensors. The extracted dialysis liquid creates low pressure in this portion of the circuit which causes a quantity of liquid coming from the blood to pass through the semi-permeable membrane of the haemodialyser. The quantity of ultrafiltrate coming from the blood will equal the quantity of the dialysis liquid extracted from the circuit 5 by the pump 17 when the portion of the low pressure circuit is non-deformable.

The functioning of the artificial kidney according to the diagram of FIG. I is as follows. Initially, the two sensors 6, 7 are calibrated as follows. Pump 10 is stopped, and valve 11 is closed and valve 12 opened. The haemodialyser and the ultrafiltration circuit are then by-passed. The dialysis liquid displaced by the pump 9 flows in the by-pass circuit along ABEF. During this calibration stage, the quantity of dialysis liquid circulating in the upline sensor 6 is strictly equal to the quantity of the dialysis liquid circulating in the downline sensor 7 since there cannot occur any loss or gain of dialysis liquid at any point of this circuit.

However, even if two sensors of the same type are used upline and downline, slight differences may exist as between one sensor and the other and the signal emitted by one of the sensors is not always strictly identical with the signal emitted by the other sensor during the same period. Thus, for example, in the case where vane flowmeters are used as sensors, the number of pulses emitted by one flowmeter may vary from the number of pulses emitted during the same period by the other flowmeter by as much as 6 to 7 percent. The calibration allows this drawback to be remedied. It also makes it possible to use two sensors of various types upline and downline. For this purpose, the counter 30 counts the number of pulses emitted by the upline sensor 6, and during the same period, the number of pulses emitted by the downline sensor 7. The two count values are transmitted to computer 32 which determines the correction coefficient which may, by way of example and not limitation, be the ratio of the number of pulses counted by one of the counters to the number of pulses counted by the other counter during the same period. The correction coefficient is stored in memory 33. The correction of the measurements effected subsequently by this coefficient makes it possible to overcome the errors due to the make up of the flowmeters.

After calibration, valve 11 is opened and valve 12 is closed. The dialysis liquid then circulates in the whole of the circuit 5 ABCDEF and in particular in the compartment 2 of the haemodialyser. The quantities of the dialysis liquid delivered by the pump 9 remains preferably equal to the quanitities delivered during calibration, and the operation of the extraction pump 17 is adjusted to the values chosen for the quantities of ultrafiltrate that one wishes to collect.

The pulses emitted by the upline sensor 6 are counted by the counter 30, those emitted by the downline sensor 7 are counted by the counter 31 during the same period. The count values are transmitted to corrector 34 which advantageously only corrects one count value in relation to the other in accordance with the correction coefficient determined by computer 32 during the calibration and stored at 33. The count value which is corrected can be that of counter 30 or that of counter 31.

Comparator 35 then compares the number of pulses coming from the upline sensor 6 and the number of pulses coming from the downline sensor 7 during the same period. Comparator 35 can, for instance, work out the difference or the ratio between the number of pulses coming from the upline sensor 6 and the number of pulses coming from the downline sensor 7. The result of this comparison of error signal is transmitted to monitor 36 which compares the error signal with its reference value "0" for a comparison based on difference, "1" for a comparison by means of a ratio. Depending on the difference between the error signal and the reference value, monitor 36 regulates the operation of pump 9, 10 so as to maintain the number of pulses counted by counter 30 equal, after correction, to the number of pulses counted by counter 31 during the same period. This results in maintaining the quantities of the dialysis liquid circulating in the upline sensor 6 equal to the quantities of dialysis liquid circulating in the downline sensor 7 during the same period.

Another embodiment of the artificial kidney is accordance with the invention is that represented in the diagram of FIG. III.

The artificial kidney in accordance with the embodiment comprises: an upline sensor 6, an upline pump 9, a downline sensor 7, a downline pump 10, a by-pass circuit 13, and a control device 8. The set constituted in the previously described embodiment shown in FIG. I by the two valves 11,12, is here replaced by one three-way valve 19 disposed at point B, downline from the pump 9 and upline from the haemodialyser 3 at the intersection with the by-pass circuit 13. The operation of this valve 19 makes it possible to select the passage for the dialysis liquid either in the by-pass circuit 13 or in the haemodialyser 3. In accordance with this embodiment, the dialysis liquid circuit comprises, moreover, a means for eliminating any bubbles present in the dialysis liquid. As embodied herein, this degassing device is constituted, for instance, by a small reservoir 20 which is open to the atmosphere on the dialysis liquid circuit.

The level of the dialysis liquid in the reservoir may vary within limits determined by the position of high and low level electrodes 23 and 24, respectively. The level of the dialysis liquid is maintained within these limits by means of a pump 18 controlled by the level of the dialysis liquid in the reservoir. Thus, when the level of the dialysis liquid in the reservoir reaches high level electrode 23, the latter actuates a slowing down of the action of the pump 18. Conversely, when the level of the dialysis liquid reachs low level electrode 24, the latter actuates an acceleration of the action of the pump 18. In general, the possible variation in the volume of the dialysis liquid between the high level and low level does not exceed 2 to 3 ml.

The opening of the dialysis liquid circuit to the atmosphere allows the elimination of the gas bubbles present in the dialysis liquid. Thus, when a quantity of the dialysis liquid is drawn off by pump 17, which will be replaced by an equal quantity of ultrafiltrate coming from the blood, one has the assurance of only drawing dialysis liquid off and not a mixture of liquid and gas bubbles. Moreover, when the sensors used for measuring the quantities of dialysis liquid are volumetric flowmeters, the dialysis liquid may be degassed to obtain an accurate measurement with the sensors.

In accordance with still another embodiment of the artificial kidney of the present invention, represented in the diagram of FIG. IV, the dialysis liquid is extracted from circuit 5 at the level of the degassing device by means of pump 17. The level of the dialysis liquid in the reservoir 20 is controlled by electrodes as previously described. The operation of the extraction pump 17 makes it possible to maintain a constant level of the dialysis liquid in reservoir 20 and to extract a portion of the dialysis liquid simultaneously. The quantity of the dialysis liquid extracted which is considered equal to the quantity of ultrafiltrate withdrawn from the blood, is measured by any known means, for instance, with a test vessel. Tests effected in this embodiment of the invention have provided the following results.

In ten tests effected by causing the dialysis liquid to circulate at 500 ml/minute over 4 hours, it was possible to measure the total quantity of the dialysis liquid circulating in the circuit 5, that is to say 120 liters, within approximately plus or minus 20 ml, that is to say, an average error of plus or minus 5 ml/h. These results allow the previously noted accuracy requirements concerning the control of ultrafiltration to be met.

Still another embodiment of the artificial kidney according to the invention is represented in the diagram of FIG. V. In this case, the ultrafiltration is not imposed by a low pressure created in the compartment 2 of the haemodialyser by an extraction of a portion of the dialysis liquid from circuit 5, but, rather, by increasing the blood pressure in the compartment 1 of the haemodialyser by any known means.

Since the quantities of the dialysis liquid circulating in upline sensor 6 are kept equal to the quantities of the dialysis liquid circulating in downline sensor 7 during the same period, the excess of the dialysis liquid coming from the ultrafiltration of the blood can flow out by overflowing at the level of the degassing reservoir 20. The quantity of the dialysis liquid that has overflowed is measured, which is considered to be equal to the ultrafiltrate quantity coming from the blood.

Still another embodiment of the present invention is represented in FIG. VI. In this embodiment there is disposed upline from the haemodialyser, not a pump 9 but a hydraulic valve 22 constituted for instance, by a variable clamp or a governed valve. By-pass circuit 13 connects the upline portion of the dialysis liquid circuit comprised between upline sensor 6 and hydraulic valve 22 to the downline portion of the dialysis liquid circuit comprised between haemodialyser 3 and pump 10. In this mode of embodiment, it is desirable to dispose upline from upline sensor 6, a device, for instance a pump, or gravity tank (not shown) to impart, if required, sufficient additional pressure to the dialysis liquid circulating in the upline sensor 6.

With continued reference to FIG. VI, a valve 11 is disposed on the dialysis liquid circuit downline from the point B and upline from hydraulic valve 22. Another valve 21 is disposed downline from haemodialyser 3 and upline from the point E. A third valve 12 is disposed on the by-pass circuit 13.

During calibration, valve 12 is opened and valves 11 and 21 are closed. The quantities of the dialysis liquid circulating in upline and downline sensors 6,7 are determined by the operation of pump 10. Then valve 12 is closed and valves 11,21 are opened. The control device 8 controls the hydraulic valve 22 to maintain the quantities of the dialysis liquid circulating in the upline sensor 6 equal to the quantities of the dialysis liquid circulating in the downline sensor 7.

According to another embodiment of the invention represented in FIG. VII, the dialysis liquid extracted from the circuit 5 by the pump 17 is reinjected into the dialysis liquid circuit upline from the upline sensor 6.

Amongst the sensors suitable for the implementation of the present invention, various other flowmeters will be apparent to one skilled in the art which can be used on the dialysis liquid circuit, and in particular, such flowmeters may be electromagnetic, thermal, ultrasonic, gear or Coriolis effect flowmeters.

Additional advantages and modifications will readily occur to those skilled in the art. The invention in its broader aspects is, therefore, not limited to the specific details, representative apparatus and illustrative example shown and described. Accordingly, departures may be made from such details without departing from the spirit or scope of the general inventive concept as defined by the appended claims and their equivalents.

What is claimed is:

1. A method for controlling and maintaining the parity of dialysis liquid quantities at the inlet and outlet of a dialysis liquid circuit connected to a haemodialyser, the dialysis liquid circuit having sensing means, positioned upline and downline of the haemodialyser, for measuring the quantity of the circulating dialysis liquid, and at least one means for displacing the dialysis liquid, comprising the steps of:

measuring, with the upline sensing means, the quantity of dialysis liquid flowing at the inlet of the liquid circuit;

measuring, with the downline sensing means and concurrently with measuring the flow in the upline sensing means, the quantity of dialysis liquid flowing at the outlet of the liquid circuit;

generating signals in accordance with the measured flows in the upline and downline sensing means;

comparing the signals representative of the flow through the upline sensing means and the flow through the downline sensing means and generating a signal in accordance with the comparison of the measured quantities of dialysis liquid; and controlling the operation of said at least one means for displacing the dialysis liquid in response to the signal representative of the comparison of the quantities of dialysis liquid flowing through the upline sensing means and the downline sensing means.

2. The method according to claim 1, including the further step of extracting, at an extraction connection in the dialysis liquid circuit, an quantity of dialysis liquid substantially equal to the quantity of ultrafiltrate withdrawn from the blood.

3. A method for controlling and maintaining the parity of dialysis liquid quantities at the inlet and outlet of a dialysis liquid circuit connected to a haemodialyser, the dialysis liquid circuit having sensing means, positioned upline and downline of the haemodialyser, for measuring the quantity of the circulating dialysis liquid, and at least one means for displacing the dialysis liquid, the method comprising the steps of:

measuring, with the upline sensing means, the quantity of dialysis liquid flowing at the inlet of the liquid circuit;

measuring, with the downline sensing means and concurrently with measuring the flow in the upline sensing means, the quantity of dialysis liquid flowing at the outlet of the liquid circuit;

generating signals in accordance with the measured flows in the upline and downline sensing means;

comparing the signals representative of the flow through the upline sensing means and the flow through the downline sensing means and generating a signal in accordance with the comparison of the measured quantities of dialysis liquid;

controlling the operation of said at least one means for displacing the dialysis liquid in response to the signal representative of the comparison of the quantities of dialysis liquid flowing through the upline sensing means and the downline sensing means;

eliminating, with the isolation means, flow through the haemodialyser such that all liquid flow through the upline sensing means passes through the downline sensing means; and calibrating the upline sensing means and downline sensing means in accordance with the signal representative of the comparison of the respective measured quantities of dialysis liquid.

4. A method for controlling and maintaining the parity of dialysis liquid quantities at the inlet and outlet of a dialysis liquid circuit connected to a haemodialyser, the dialysis liquid circuit having sensing means, positioned upline and downline of the haemodialyser, for measuring the quantity of the circulating dialysis liquid, and at least one means for displacing the dialysis liquid, the method comprising the steps of:

measuring, with the upline sensing means, the quantity of dialysis liquid flowing at the inlet of the liquid circuit;

measuring, with the downline sensing means and concurrently with measuring the flow in the upline sensing means, the quantity of dialysis liquid flowing at the outlet of the liquid circuit;

generating signals in accordance with the measured flows in the upline and downline sensing means;

comparing the signals representative of the flow through the upline sensing means and the flow through the downline sensing means and generating a signal in accordance with the comparison of the measured quantities of dialysis liquid;

controlling the operation of said at least one means for displacing the dialysis liquid in response to the signal representative of the comparison of the quantities of dialysis liquid flowing through the upline sensing means and the downline sensing means;

extracting, at an extraction connection in the dialysis liquid circuit, a quantity of dialysis liquid substantially equal to the quantity of ultrafiltrate withdrawn from the blood;

eliminating, with the isolation means, flow through the haemodialyser and the extraction connection such that all liquid flow through the upline sensing means passes through the downline sensing means; and calibrating the upline and downline sensing means in accordance with the signal representative of the comparison of the respective measured quantities of dialysis liquid.

5. An artificial kidney comprising a haemodialyser containing at least a first and a second compartment separated by a semi-permeable membrane for permitting dialysis and ultrafiltration of the blood, said first compartment being connected to a patient by an extracorporeal blood circuit, and said second compartment being connected to a dialysis liquid circuit;

means for displacing the dialysis liquid through the circuit, and an upline and downline sensing means, positioned on opposite sides of said second compartment in said liquid circuit, for measuring the quantity of dialysis liquid flowing upline and downline of said haemodialyser and generating signals in accordance with said measured flows;

means for comparing the signals representative of flow in the upline.sensing means and the flow in the downline sensing means during the same measurement period, and for generating a signal in accordance with said comparison of the measured quantities of dialysis liquid; and means for controlling the operation of said displacing means in response to the signal representative of the comparison of the quantities of dialysis liquid measured with said upline sensing means and said downline sensing means.

6. An artificial kidney comprising a haemodialyser containing at least a first and a second compartment separated by a semi-permeable membrane for permitting dialysis and ultrafiltration of blood, said first compartment being connected to a patient by an extracorporeal blood circuit, and said second compartment being connected to a dialysis liquid circuit;

means for displacing the dialysis liquid through the circuit, and an upline and downline sensing means, positioned on opposite sides of said second compartment in said liquid circuit, for measuring the quantity of dialysis liquid flowing upline and downline of said haemodialyser and generating signals in accordance with said measured flows;

means for comparing the signals representative of flow in the upline sensing means and the flow in the downline sensing means during the same measurement period, and for generating a signal in accordance with said comparison of the measured quantities of dialysis liquid;

means for controlling the operation of said displacing means in response to the signal representative of the comparison of the quantities of dialysis liquid measured with said upline sensing means and said downline sensing means; and wherein said means for displacing the dialysis liquid includes a first and second pump means, said first pump means being positioned upline of said haemodialyser and said second pump means being positioned downline of said haemodialyser.

7. An artificial kidney comprising a haemodialyser containing at least a first and a second compartment separated by a semi-permeable membrane for permitting dialysis and ultrafiltration of blood, said first compartment being connected to a patient by an extracorporeal blood circuit, and said second compartment being connected to a dialysis liquid circuit;

means for displacing the dialysis liquid through the circuit, and an upline and downline sensing means, positioned on opposite sides of said second compartment in said liquid circuit, for measuring the quantity of dialysis liquid flowing upline and downline of said haemodialyser and generating signals in accordance with said measured flows;

means for comparing the signals representative of flow in the upline sensing means and the flow in the downline sensing means during the same measurement period, and for generating a signal in accordance with said comparison of the measured quantities of dialysis liquid;

means for controlling the operation of said displacing means in response to the signal representative of the comparison of the quantities of dialysis liquid measured with said upline sensing means and said downline sensing means; and means for withdrawing a portion of the dialysis liquid flowing through the circuit at an extraction connection, said withdrawn portion being substantially equal to the quantity of ultrafiltrate withdrawn from the blood.

8. An artificial kidney according to claim 7 including means for isolating said haemodialyser and said extraction connection such that when said haemodialyser and extraction connection are isolated all the liquid flow through said upline sensor flows through said downline sensor; and means for determining and recording a correction coefficient for calibrating said sensors in accordance with said measured flows in said upline and downline sensors when said haemodialyser and said extraction connection are isolated.

9. An artificial kidney according to claim 7, wherein said means for withdrawing a portion of the dialysis liquid includes a pump means for drawing off said portion of dialysis liquid.

10. An artificial kidney according to claims 5, 6, 7 or 9 wherein said means for displacing the dialysis liquid is an occluding pump.

11. An artificial kidney according to claims 5, 6, 7 or 9 wherein said upline and downline sensing means for measuring the quantities of the circulating dialysis liquid include means for generating pulses, each pulse corresponding to the passage of a predetermined quantity of dialysis liquid through said respective sensing means.

12. An artificial kidney comprising a haemodialyser containing at least a first and a second compartment separated by a semi-permeable membrane for permitting dialysis and ultrafiltration of the blood, said first compartment being connected to a patient by an extracorporeal blood circuit, and said second compartment being connected to a dialysis liquid circuit;

means for displacing the dialysis liquid through the circuit, and an upline and downline sensing means, positioned on opposite sides of said second compartment in said liquid circuit, for measuring the quantity of dialysis liquid flowing upline and downline of said haemodialyser and generating signals in accordance with said measured flows;

means for comparing the signals representative of flow in the upline sensing means and the flow in the downline sensing means during the same measurement period, and for generating a signal in accordance with said comparison of the measured quantities of dialysis liquid;

means for controlling the operation of said displacing means in response to the signal representative of the comparison of the quantities of dialysis liquid measured with said upline sensing means and said downline sensing means; and means for isolating the haemodialyser such that when said haemodialyser is isolated all the liquid flow through said upline sensor flows through said downline sensor, and means for determining and recording a correction coefficient for calibrating said sensors in accordance with said measured flows in said upline and downline sensors when said haemodialyser is isolated.

13. An artificial kidney according to claims 5, 6, 7, 9, 12 or 8 including means, selectively positioned in said liquid circuit, for eliminating any gas bubbles present in the dialysis liquid.

14. An artificial kidney, comprising:
a haemodialyser containing at least a first and a second compartment separated by a semi-permeable membrane for permitting dialysis and ultrafiltration of the blood, said first compartment being connected to a patient by an extracorporeal blood circuit, and said second compartment being connected to a dialysis liquid circuit;
means for displacing the dialysis liquid through the circuit, and an upline and downline sensing means, positioned on opposite sides of said second compartment in said liquid circuit, for measuring the quantity of dialysis liquid flowing upline and downline of said haemodialyser and generating signals in accordance with said measured flows;
means for comparing the signals representative of flow in the upline sensing means and the flow in the downline sensing means during the same measurement period, and for generating a signal in accordance with said comparison of the measured quantities of dialysis liquid;
means for controlling the operation of said displacing means in response to the signal representative of the comparison of the quantities of dialysis liquid measured with said upline sensing means and said downline sensing means;
said upline and downline sensing means including means for generating pulses, each pulse corresponding to the passage of a predetermined quantity of dialysis liquid through said respective sensing means, and further including means for counting and recording said pulses emitted by said sensing means, and comparing the recorded number of pulses of each said sensing means during the same time period.

15. An artificial kidney according to claim 14, wherein said means for displacing the dialysis liquid includes a first and second pump means, said first pump means being positioned upline of said haemodialyser and said second pump means being positioned downline of said haemodialyser.

16. An artificial kidney according to claim 14, including means for withdrawing a portion of the dialysis liquid flowing through the circuit at an extraction connection.

17. An artificial kidney according to claim 16, wherein said means for withdrawing a portion of the dialysis liquid includes a pump means for drawing off said portion of dialysis liquid.

18. An artificial kidney comprising a haemodialyser containing at least a first and a second compartment separated by a semi-permeable membrane for permitting dialysis and ultrafiltration of blood, said first compartment being connected to a patient by an extracorporeal blood circuit, and said second compartment being connected to a dialysis liquid circuit;
means for displacing the dialysis liquid through the circuit, and an upline and downline sensing means, positioned on opposite sides of said second compartment in said liquid circuit, for measuring the quantity of dialysis liquid flowing upline and downline of said haemodialyser and generating signals in accordance with said measured flows;
means for comparing the signals representative of flow in the upline sensing means and the flow in the downline sensing means during the same measurement period, and for generating a signal in accordance with said comparison of the measured quantities of dialysis liquid;
means for controlling the operation of said displacing means in response to the signal representative of the comparison of the quantities of dialysis liquid measured with said upline sensing means and said downline sensing means; and
means for calibrating said upline and downline sensing means.

* * * * *